(12) United States Patent
Jan et al.

(10) Patent No.: US 10,160,699 B1
(45) Date of Patent: Dec. 25, 2018

(54) LIGHT OLEFIN AND AROMATICS PROCESSES INCORPORATING HYDROGEN SELECTIVE MEMBRANES

(71) Applicant: UOP LLC, Des Plaines, IL (US)

(72) Inventors: Deng-Yang Jan, Elk Grove Village, IL (US); Chunqing Liu, Arlington Heights, IL (US); Xueliang Dong, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/989,300

(22) Filed: May 25, 2018

(51) Int. Cl.
*C07C 5/41* (2006.01)
*C07C 5/333* (2006.01)
*C07C 2/08* (2006.01)

(52) U.S. Cl.
CPC .............. *C07C 5/41* (2013.01); *C07C 2/08* (2013.01); *C07C 5/333* (2013.01)

(58) Field of Classification Search
CPC ..... C07C 11/02; C07C 5/3337; C07C 5/3335; C07C 7/144; C07C 2523/26; C07C 2523/42; C07C 5/321; C07C 5/325; C07C 5/04; B01D 53/22; B01D 2256/24; B01D 2257/108; B01J 23/58; B01J 23/62; B01J 29/068; B01J 29/035; B01J 29/06; B01J 29/40; B01J 29/44; B01J 29/70; B01J 29/7007; B01J 29/7034; B01J 29/7415; B01J 29/86; B01J 37/0009
See application file for complete search history.

(56) References Cited

U.S. PATENT DOCUMENTS

| 4,313,013 A | 1/1982 | Harris |
| 4,788,371 A | 11/1988 | Imai et al. |
| 4,926,005 A | 5/1990 | Olbrich et al. |
| 5,430,218 A * | 7/1995 | Miller .................. C07C 5/3337 585/654 |
| 5,516,961 A | 5/1996 | Miller et al. |
| 9,776,935 B2 * | 10/2017 | Palo ..................... C07C 5/3335 |
| 2014/0018594 A1 | 1/2014 | Palo et al. |

OTHER PUBLICATIONS

Seok-Jhin Kim, et al., Thin Hydrogen-Selective SAPO-34 Zeolite Membranes for Enhanced Conversion and Selectivity in Propane Dehydrogenation Membrane Reactors, Chem. Mater., 2016, 28, 4397-4402.

Ivo F.J. Vankelecom, Polymeric Membranes in Catalytic Reactors, Chem. Rev., 2002, 102, 3779-3810.

* cited by examiner

*Primary Examiner* — Sharon Pregler

(57) ABSTRACT

A catalytic reactor and membrane separation process is described in which a hydrocarbon feed comprising at least one alkane or alkylaromatic is at least one of dehydrogenated, dehydrocyclized, or dehydrocyclodimerized in first and second reactors. The reaction mixtures are separated in first and second membrane separation zones using first and second small pore microporous inorganic non-metallic membrane with a pore size of less than or equal to 4 Å at a temperature of greater than 500° C. The membrane separation zones are separate from the reactors.

20 Claims, 1 Drawing Sheet

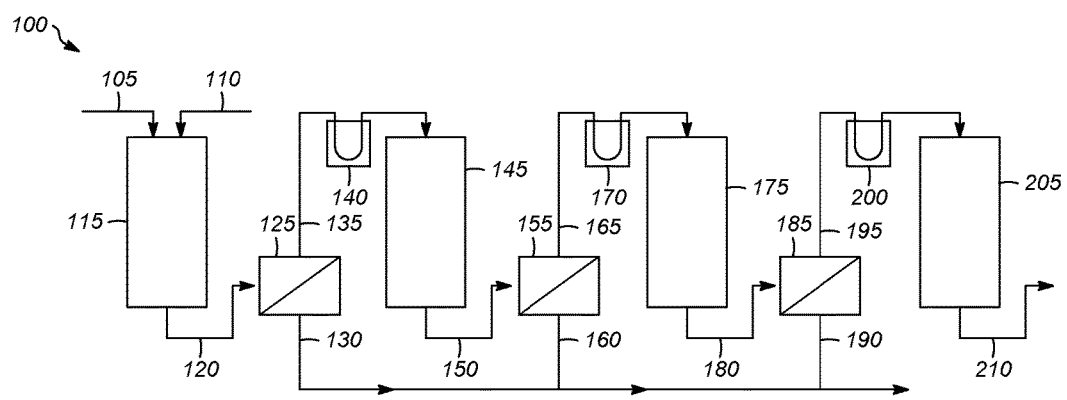

LIGHT OLEFIN AND AROMATICS PROCESSES INCORPORATING HYDROGEN SELECTIVE MEMBRANES

BACKGROUND

Dehydrogenation, dehydrocyclization, and dehydrocyclodimerization processes involve the removal of hydrogen from hydrocarbons to form alkenes and/or aromatics. The olefin and aromatics yields and throughputs are constrained by thermodynamic limitations, including endothermic and $H_2$ formation. Specifically, they are limited by the amount of heat that can be introduced without causing significant thermal cracking, and by how low the operating pressures can be without incurring excess compression cost (capital and utility).

One solution to the problem of hydrogen formation is to oxidize it. For example, U.S. Pat. No. 4,788,371 describes a dehydrogenation process which includes selective oxidation of the hydrogen produced which is used to generate heat to increase the temperature to the level needed for the next dehydrogenation reaction section. A single catalyst was used for both dehydrogenation and oxidation. The reaction could be performed in a reactor with multiple beds or in different reactors for the dehydrogenation and oxidation reactions. The need to add oxygen or air handling equipment increased the cost of the process. In addition, the oxidation produced water which had to be removed.

Another solution was the use of catalytic membrane reactors which combine chemical reactions with membrane separation. The membranes can be polymeric, metallic, and inorganic. However, the use of catalytic membrane reactors makes the process more complex, and more difficult to model and optimize due to the combined reaction and separation processes. Polymeric Membranes in Catalytic Reactors, Chem. Rev. 2002, 102, 3779-3810; Thin Hydrogen-Selective SAPO-34 Zeolite Membranes for Enhanced Conversion and Selectivity in Propane Dehydrogenation Membrane Reactors, Chem. Mater. 2016, 28, 4397-4402.

U.S. Pat. No. 9,776,935 describes a process involving dehydrogenation and membrane separation. The dehydrogenation reaction mixture is subjected to membrane separation in a separate unit. The use of separate units for dehydrogenation and membrane separation is said to allow independent control of the process conditions in each unit. In order to avoid problems with the stability of the membranes, the membrane separation unit is maintained slightly below 500° C., preferably in the range of 420-490° C., and more preferably 450-470° C. The dehydrogenation reaction takes place at temperatures of 450-750° C., preferably 500-750° C., and most preferably 550-750° C. to attain techno-economically viable conversions per pass to minimize the capital and operating cost to purify the product and recycle the unconverted hydrocarbon, respectively. Operating the membrane separation unit at less than 500° C. requires additional interstage heating to increase the retentate to the dehydrogenation conditions of the next reactor. It could also require cooling the reaction mixture to obtain the desired separation temperature. These steps increase the overall cost of the process and incur additional thermal cracking.

Therefore, there is a need for a process for making olefins, aromatics, and alkenylaromatics in which the temperature of the reaction mixture is maintained at reaction conditions during the separation process.

BRIEF DESCRIPTION OF THE DRAWING

The FIGURE is an illustration of one embodiment of the process.

SUMMARY AND DESCRIPTION OF THE INVENTION

Recent advances in membranes, such as small pore microporous inorganic non-metallic membranes, enable hydrogen to be removed from hydrocarbon streams in a controlled and cost effective manner under elevated process conditions, such as temperatures greater than 500° C. Incorporating this membrane technology into dehydrogenation, dehydrocyclization, and dehydrocyclodimerization processes de-bottlenecks olefin and aromatics producing processes. Significant increases in olefin and aromatics production throughput can be realized by at least partially removing hydrogen produced in the processes, which results in increased conversion and less compression required, reducing capital and operating costs for both the reaction section and the separation section.

One aspect of the invention is a catalytic reactor and membrane separation process. In one embodiment, the process comprises providing a hydrocarbon feed comprising at least one alkane or alkylaromatic. The hydrocarbon feed is at least one of dehydrogenated, dehydrocyclized, or dehydrocyclodimerized in a first reactor in the presence of a first catalyst under first reaction conditions to form a first reaction mixture comprising at least one first alkene, aromatic, alkenylaromatics, or mixtures thereof, unreacted alkane or alkylaromatic, and hydrogen. The first reaction mixture is separated in a first membrane separation zone using a first small pore microporous inorganic non-metallic membrane with a pore size of less than or equal to 4 Å at a temperature of greater than 500° C. into a first permeate comprising hydrogen and a first retentate comprising at least one first alkene, aromatic, alkenylaromatic, or mixtures thereof, unreacted alkane or alkylaromatic, and hydrogen, and wherein the first membrane separation zone is separate from the first reactor. The first reaction mixture is heated before separating the first reaction mixture in the first membrane separation zone, or the first retentate is heated after separating the first reaction mixture in the first membrane separation zone. The first retentate is at least one of dehydrogenated, dehydrocyclized, and dehydrocyclodimerized in a second reactor in the presence of a second catalyst under second conditions to form a second reaction mixture comprising at least one second alkene, aromatic, alkenylaromatic, or mixtures thereof, the at least one first alkene, aromatic, alkenylaromatic, or mixtures thereof, unreacted alkane or alkylaromatic, and hydrogen. The second reaction mixture is separated in a second membrane separation zone using a second small pore microporous inorganic non-metallic membrane with a pore size of less than or equal to 4 Å at a temperature of greater than 500° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, unreacted alkane or alkylaromatic, and hydrogen, and wherein the second membrane separation zone is separate from the second reactor.

When the hydrogen is separated from the reaction mixture using the small pore microporous inorganic non-metallic membrane, at least a portion of the hydrogen is removed from the reaction mixture. The amount of hydrogen removed from the reaction mixture is typically 20 mol % to 99 mol % of the hydrogen produced in the reaction. The purity of the hydrogen in the permeate is generally 80 mol % or more, or 85 mol % or more, or 90 mol % or more, or 95 mol % or more.

In some embodiments, at least one of the first or second small pore microporous inorganic non-metallic membranes comprises a silica membrane, a ceramic membrane, or a molecular sieve membrane. In some embodiments, at least one of the first or second small pore microporous inorganic non-metallic membranes comprises a molecular sieve membrane selected from AlPO-14, AlPO-18, AlPO-34, SAPO-34, a CHA type molecular sieve, SSZ-13, DDR, ITQ-12, CDS-1, UZM-25, or combinations thereof.

In some embodiments, at least one of separating the first reaction mixture or separating the second reaction mixture takes place at the temperature of at least 550° C.

In some embodiments, the process further comprises heating the second reaction mixture or the second retentate. The second retentate is at least one of dehydrogenated, dehydrocyclized, and dehydrocyclodimerized in a third reactor in the presence of a third catalyst under third reaction conditions to form a third reaction mixture comprising at least one third alkene, aromatic, alkenylaromatic, or mixtures thereof, the at least one second alkene, the at least one first alkene, aromatic, alkenylaromatic, or mixtures thereof, unreacted alkane or alkylaromatic, and hydrogen. The third reaction mixture is separated in a third membrane separation zone using a third small pore microporous inorganic non-metallic membrane with a pore size of less than or equal to 4 Å at a temperature of greater than 500° C. into a third permeate comprising hydrogen and a third retentate comprising the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, unreacted alkane or alkylaromatic, and hydrogen, and wherein the third membrane separation zone is separate from the third reactor.

In some embodiments, the process further comprises at least one of dehydrogenating, dehydrocyclizing, and dehydrocyclodimerizing the third retentate in a fourth reactor in the presence of a catalyst under fourth reaction conditions to form a fourth reaction mixture comprising at least one fourth alkene, aromatic, alkenylaromatic, or mixtures thereof, the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, the unreacted alkane or alkylaromatic, and hydrogen.

In some embodiments, the hydrocarbon feed comprises at least one alkane containing 2 to 12 carbon atoms, and wherein the first reaction mixture comprises the at least one first alkene having a same number of carbon atoms as the at least one alkane in the hydrocarbon feed and wherein the second reaction mixture comprises at least one second alkene having a same number of carbon atoms as the at least one alkane in the hydrocarbon feed.

In some embodiments, the hydrocarbon feed comprises the at least one alkane containing 2 to 4 carbon atoms. The hydrocarbon feed is dehydrogenated in the first reactor. The reaction conditions include at least one of a temperature in a range of 500 to 1000° C., and pressure in a range of 0 to 1379 kPa, and the first reaction mixture comprises at least first one alkene having a same number of carbon atoms as the at least one alkane in the hydrocarbon feed. The first reaction mixture is dehydrogenated in the second reactor. The reaction conditions include at least one of a temperature in a range of 500 to 1000° C., and pressure in a range of 0 to 1379 kPa, and the second reaction mixture comprises at least one second alkene having a same number of carbon atoms as the at least one alkane in the hydrocarbon feed.

In some embodiments, the hydrocarbon feed comprises the at least one alkane containing 6 to 12 carbon atoms. The hydrocarbon feed is dehydrocyclized in the first reactor. The reaction conditions include at least one of a temperature in a range of 400 to 650° C., and pressure in a range of 0 to 1379 kPa, and the first reaction mixture comprises at least first one aromatic having a same number of carbon atoms as the at least one alkane in the hydrocarbon feed. The reaction mixture is dehydrocyclized in the second reactor. The reaction conditions include at least one of a temperature in a range of 400 to 650° C., and pressure in a range of 0 to 1379 kPa, and the second reaction mixture comprises at least one second aromatic having a same number of carbon atoms as the at least one alkane in the hydrocarbon feed.

In some embodiments, the hydrocarbon feed comprises the at least one alkane containing 1 to 7 carbon atoms. The hydrocarbon feed is dehydrocyclodimerized in the first reactor, and the reaction conditions include at least one of a temperature in a range of 400 to 1000° C., and pressure in a range of 0 to 1379 kPa. The reaction mixture is dehydrocyclodimerized in the second reactor, and the reaction conditions include at least one of a temperature in a range of 400 to 1000° C., and pressure in a range of 0 to 1379 kPa.

In some embodiments, the unreacted alkane is separated from at least one of the first reaction mixture and the second reaction mixture.

In some embodiments, the separated unreacted alkane or alkylaromatic is recycled to at least one of the first reactor or the second reactor.

In some embodiments, at least one of the first reaction conditions or the second reaction conditions comprises at least one of a temperature of 500 to 1200° C., and a pressure in a range of 0 to 1379 kPa, and a space velocity of 0.1 to 10 $hr^{-1}$ WHSV.

In some embodiments, the hydrocarbon feed comprises 0 to 70 mol % of hydrogen, or 20 to 70 mol %.

In some embodiments, the amount of hydrogen removed from the first or second reaction mixture is 20 mol % to 99 mol % of the hydrogen produced in the dehydrogenation, dehydrocyclization, and dehydrocyclodimerization reaction.

In some embodiments, the purity of the hydrogen in the first or second permeate is 80 mol % or more.

In another embodiment, the process comprises providing a hydrocarbon feed comprising at least one alkane or alkylaromatic. The hydrocarbon feed is at least one of dehydrogenated, dehydrocyclized, or dehydrocyclodimerized in a first reactor in the presence of a first catalyst under first reaction conditions to form a first reaction mixture comprising at least one first alkene, aromatic, alkenylaromatics, or mixtures thereof, unreacted alkane or alkylaromatic, and hydrogen. The first reaction mixture is separated in a first membrane separation zone using a first small pore microporous inorganic non-metallic membrane with a pore size of less than or equal to 4 Å at a temperature of greater than 550° C. into a first permeate comprising hydrogen and a first retentate comprising at least one first alkene, aromatic, alkenylaromatic, or mixtures thereof, unreacted alkane or alkylaromatic, and hydrogen, and wherein the first membrane separation zone is separate from the first dehydrogenation reaction zone. The first reaction mixture is heated before separating the first reaction mixture in the first membrane separation zone, or the first retentate is heated after separating the first reaction mixture in the first membrane separation zone. The first retentate is at least one of dehydrogenated, dehydrocyclized, and dehydrocyclodimerized in a second reaction zone in the presence of a second catalyst under second conditions to form a second reaction mixture comprising at least one second alkene, aromatic, alkenylaromatic, or mixtures thereof, the at least one first alkene, aromatic, alkenylaromatic, or mixtures thereof, unreacted alkane or alkylaromatic, and hydrogen. The second reaction mixture is separated in a second membrane separation zone using a second small pore microporous inorganic non-metallic membrane with a pore size of less than or equal to 4 Å at a temperature of greater than 550° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, unreacted alkane or alkylaromatic, and hydrogen, and wherein the second membrane separation zone is separate from the second reactor. At least one of the first or second small pore microporous inorganic non-metallic membranes comprises a molecular sieve membrane selected from AlPO-14, AlPO-18, AlPO-34, SAPO-34, a CHA type molecular sieve, SSZ-13, DD3R, ITQ-12, CDS-1, UZM-25, or combinations thereof.

In some embodiments, the unreacted alkane is separated from at least one of the first reaction mixture and the second reaction mixture.

In some embodiments, the separated unreacted alkane or alkylaromatic is recycled to at least one of the first reactor or the second reactor.

In some embodiments, at least one of the first reaction conditions or the second reaction conditions comprises at least one of a temperature of 500 to 1200° C., and a pressure in a range of 0 to 1379 kPa, and a space velocity of 0.1 to 10 $hr^{-1}$ WHSV.

The membrane separation zones comprise small pore microporous inorganic non-metallic membranes with a pore size of less than or equal to 4 Å, or a pore size of 2.5-3.8 Å. The small pore microporous inorganic non-metallic membranes can be a silica membrane, a ceramic membrane, or a molecular sieve membrane including, but not limited to, a zeolite membrane, and a non-zeolite membrane. Any suitable small pore microporous inorganic non-metallic membrane with a pore size of less than or equal to 4 Å can be used. Suitable small pore microporous inorganic non-metallic membrane with a pore size of less than or equal to 4 Å include, but are not limited to, a silica membrane, a ceramic membrane, and a molecular sieve membrane. Suitable molecular sieve membranes include, but are not limited to, AlPO-14, AlPO-18, AlPO-34, SAPO-34, a CHA type molecular sieve, SSZ-13, DD3R, ITQ-12, CDS-1, UZM-25, or combinations thereof.

The small pore microporous inorganic non-metallic membrane in one membrane separation zone can be the same as, or different from, the small pore microporous inorganic non-metallic membrane in another membrane separation zone.

The membrane separation zones operate at a temperature of greater than 500° C. and lower than 1000° C., or greater than 510° C., or greater than 520° C., or greater than 530° C., or greater than 540° C., or greater than 550° C. By operating the membrane separation zone at temperatures compatible with the dehydrogenation, dehydrocyclization, or dehydrocyclodimerization reactor, less interstage heating is required.

There are multiple alternating reactors and membrane separation zones with interstage heaters between adjacent reactors. The interstage heaters can be located either before or after the membrane separation zone.

There is generally one less membrane separation zone than reactor. There are typically at least three reactors and at least two membrane separation zones, or at least four reactors and at least three membrane separation zones. There can be more than four reactors and more than three membrane separation zones, if desired.

The reaction conditions generally include at least one of a temperature in a range of 400° C. to 1200° C., a pressure in a range of 0 to 1379 kPa (0 to 200 psig), or 0 to 345 kPa (0 to 50 psig), and a space velocity of 0.1 to 10 $hr^{-1}$ WHSV.

The hydrocarbon feed comprises $C_1$ to $C_{15}$ paraffins, naphthene, or alkylaromatics with alkyl groups having greater than 2 and less than 5 carbon number. The paraffins may be linear or branched, and the naphthenes comprise non-alkyl- and alkyl-substituted cyclopentane and cyclohexane. It may also contain small amounts of alkenes, and like as will be understood by those of skill in the art.

The hydrocarbon feed, operation conditions, and dehydrogenation catalyst will depend on the specific process involved.

In a light paraffin dehydrogenation process (e.g., the Oleflex™ process from UOP), $H_2$/olefin selective membranes enable the complete or partial removal of $H_2$ from the paraffin/olefin reaction mixture between reactor stages either before or after reheating the reaction mixture in the interstage heater. This will help the thermodynamics of the process by maintaining and/or lowering $P(H_2)$, which will give a higher equilibrium olefin concentration in the effluent without raising the temperatures or lowering the operating pressures. In another scenario, $H_2$/olefin selective membranes can enable complete or partial removal of $H_2$/olefin at the inter-stage reheat step. This will further help equilibrium by maintaining and/or lowering $P(H_2)$ and P(olefin), which will result in a higher overall olefin concentration and a lower coke precursor concentration.

For the light paraffin dehydrogenation process, the hydrocarbon feed will typically be $C_2$, $C_3$, $C_4$ paraffin or the mixture of thereof. In some embodiments, the feed can be ethyl benzene which can be dehydrogenated to make styrene. The operating conditions includes temperatures in the range of 500 to 1000° C., a pressure in a range of 0 to 1379 kPa, and a space velocity of 0.1 to 10 $hr^{-1}$ WHSV. The catalyst comprises a noble metal, such as platinum, palladium, and/or a Group VI element, such as chromium, molybdenum, and tungsten, supported on inorganic oxides, such as alumina, silica, magnesia or mixtures thereof. Optionally, a Group 13 element, such as indium, and gallium, and/or a Group 14 element, such as tin, and germanium or mixtures thereof can be incorporated as a modifier. Optionally, alkali and/or alkali earth metals can also be incorporated to modify and improve the catalyst activity, selectivity, and stability.

A similar approach can be used for catalytic reforming of straight run naphtha (SRN) of $C_6$-$C_{12}$ paraffins and naphthenes to aromatics, especially for $C_6$/$C_7$, by removing hydrogen at the inter-stage heating step. In some embodiments, $C_6$/$C_7$ non-aromatics are processed separately from $C_8$-$C_{10}$ non aromatics using conventional and zeolitic catalytic reforming catalysts.

For the catalytic reforming of SRN, the catalyst will typically comprise noble metals, such as platinum and palladium, and/or Group VI elements, such as chromium, and molybdenum, supported on inorganic oxides, such as alumina, silica, magnesia and mixtures thereof. The catalyst can optionally be modified by incorporating a halogen, such as chloride, an alkali, such as potassium, and/or an alkali earth, such as barium. Optionally, modifiers such as Group 14 elements, such as tin and germanium, and/or a Group 13 element, such as indium and gallium, or mixtures thereof can be incorporated as modifier. The catalyst can also comprise a noble metal supported on a zeolite, such as Zeolite LTL containing alkali and/or alkali earth cations. The operating conditions include temperatures in the range of 400 to 600° C., pressures in the range of 0 to 1379 kPa, and a space velocity of 0.1 to 10 $hr^{-1}$ WHSV.

This approach can also be applied to processes for converting LPG ($C_3/C_4$) (such as the UOP-BP Cyclar™ process) and light naphtha to aromatics. The aromatics yields and fuel gas formation in dehydrocyclodimerization is especially sensitive to $P(H_2)$. By operating at moderate pressures, the removal of $H_2$ using the $H_2$ selective membrane enables the process to be operated in a cost effective manner with improved aromatics yield and lower fuel gas ($C_1/C_2$) yield.

For processes for converting LPG and light naphtha to aromatics, the feed comprises hydrocarbons of 2 to 7 carbon atoms. The catalyst comprises zeolites, such as Zeolite Pentasil, MWW, UZM-35, UZM-39, UZM-44, TUN-9 or BEA. Optionally, the catalyst comprises a Group 12 element, such as zinc, a Group 13 element, such as gallium or indium, and/or a noble metal, or the mixtures thereof. The operating conditions include temperatures in the range of 500 to 900° C., pressures in the range of 0 to 1379 kPa, and a space velocity of 0.1 to 10 $hr^{-1}$ WHSV.

The general process 100 is illustrated in the FIGURE for dehydrogenation. The overall process is similar for light olefin dehydrogenation, catalytic reforming of straight run naphtha, and dehydrocyclodimerization, although the specific feeds, operation conditions, catalysts, reactions, and products will vary depending on the process being used, as discussed above.

The hydrocarbon feed 105 is sent to first reactor 115. The hydrocarbon feed 105 comprises at least one alkane containing 2 to 15 carbon atoms, and optionally up to 70 mol % hydrogen. An optional recycle stream 110 can also be sent to first reactor 115. The recycle stream 110 may comprise one or more of at least one olefin or aromatic or both, unreacted alkane or alkylaromatic, and hydrogen.

The at least one alkane or alkylaromatic in the hydrocarbon feed 105 and any alkane or alkylaromatic in the optional recycle stream 110 are dehydrogenated, dehydrocyclized, or dehydrocyclodimerized in the first reactor 115 forming first reaction mixture 120 which comprises at least one first olefin or aromatic or both, unreacted alkane or alkylaromatic and hydrogen. The at least one first olefin or aromatic or both corresponds to the at least one first alkane or alkylaromatic in the feed or the alkane alkylaromatic in the recycle stream (if any) (i.e., it has the same number of carbon atoms).

The first reaction mixture 120 is sent to the first membrane separation zone 125 which comprises the first small pore microporous inorganic non-metallic membrane. The first reaction mixture 120 is separated into first permeate 130 and first retentate 135. First permeate 130 comprises hydrogen. First retentate 135 comprises the at least one first olefin or aromatic or both, unreacted alkane or alkylaromatic, and hydrogen. The first membrane separation zone 125 is operated at a temperature of greater than 500° C.

First retentate 135 is heated in the first interstage heater 140 to raise the temperature and sent to the second reaction zone 145. First retentate 135 is dehydrogenated, dehydrocyclized, or dehydrocyclodimerized in second reaction zone 145 to form second reaction mixture 150 comprising at least one second olefin or aromatic or both, the at least one first olefin or aromatic or both, unreacted alkane or alkylaromatic, and hydrogen.

The second reaction mixture 150 is sent to the second membrane separation zone 155 which comprises the second small pore microporous inorganic non-metallic membrane. The second reaction mixture 150 is separated into second permeate 160 and second retentate 165. Second permeate 160 comprises hydrogen. Second retentate 165 comprises the at least second first olefin or aromatic or both, the at least one first olefin or aromatic or both, unreacted alkane or alkylaromatic, and hydrogen. The second membrane separation zone 155 is operated at a temperature of greater than 500° C.

Second retentate 165 is heated in the second interstage heater 170 to raise the temperature and sent to the third reaction zone 175. Second retentate 165 is dehydrogenated, dehydrocyclized, or dehydrocyclodimerized in third reaction zone 175 to form third reaction mixture 180 comprising at least one third olefin or aromatic or both, the at least one second olefin or aromatic or both, the at least one first olefin or aromatic or both, unreacted alkane or alkylaromatic, and hydrogen.

The third reaction mixture 180 is sent to the third membrane separation zone 185 which comprises the third small pore microporous inorganic non-metallic membrane. The third reaction mixture 180 is separated into third permeate 190 and third retentate 195. Third permeate 190 comprises hydrogen. Third retentate 195 comprises the at least one third olefin or aromatic or both, the at least second first olefin or aromatic or both, the at least one first olefin or aromatic or both, unreacted alkane or alkylaromatic, and hydrogen. The third membrane separation zone 185 is operated at a temperature of greater than 500° C.

Third retentate 195 is heated in the third interstage heater 200 to raise the temperature and sent to the fourth reactor 205. Third retentate 195 is dehydrogenated, dehydrocyclized, or dehydrocyclodimerized in fourth reactor 205 to form fourth reaction mixture 210 comprising at least one fourth olefin or aromatic or both, the at least one third olefin or aromatic or both, the at least one second olefin or aromatic or both, the at least one first olefin or aromatic or both, unreacted alkane or alkylaromatic, and hydrogen.

The fourth reaction mixture 210 from a dehydrogenation unit can be cooled, compressed, dried, and sent to a cryogenic system to separate the reaction mixture into a hydrogen-rich stream and a hydrocarbon stream. A portion of the hydrogen-rich stream can be combined with the fresh and unconverted hydrocarbon feed and sent to the reactor. The remaining portion of the hydrogen-rich stream can be purified further to recover hydrogen at greater than 99 mol % purity. Liquid coming off the cryogenic separator can be sent to selective hydrogenation to remove diolefins and acetylenes. In some embodiments, it can be sent to a deethanizer and a propane-propylene splitter to produce a chemical or polymer grade propylene. The unconverted propane can be recycled back to the reactor.

The fourth reaction mixture 210 from a dehydrocyclization unit can be cooled and sent to a separator, where hydrogen rich gas can be separated from the liquid product. A portion of the gas can be compressed and recycled to the reactor, and the net gas can be sent to the other sections of the refinery complex where hydrogen is needed. The liquid coming off the separator can be sent to a product stabilizer where the volatile hydrocarbons are fractionated from the aromatics rich liquid product.

The fourth reaction mixture 210 from a dehydrocyclodimerization can be sent to a separator. The overhead can be compressed and sent to a gas recovery section to obtain hydrogen product, fuel gas and light saturate/unconverted alkanes. The liquid product from the bottom of the separator can be sent to a stripper where $C_{5+}$ aromatic product can be recovered, and the light saturates and unconverted alkanes can be combined and recycled back to the reactor.

First permeate 130, second permeate 160, and third permeate 190 can be combined or processed separately. The permeate of the $H_2$ selective small pore microporous inorganic non-metallic membrane comprises greater than 85 mol %, or greater than 90 mol-% purity hydrogen. It can join the reactor effluent stream, before being compressed, dried, and sent to a cryogenic system. In some embodiments, it can be combined with fresh and unconverted hydrocarbon feed and recycle hydrogen coming off the cryogenic separator, and then be recycled back to the reactor. In some embodiments, the hydrogen-rich permeates are the only source of hydrogen, and they are co-fed into the reactor with fresh and unconverted hydrocarbon.

Alternatively, one or more of interstage heaters 140, 170, 200 could be located before membrane separation zones 125, 155, 185 respectively, if desired.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a catalytic reactor and membrane separation process comprising providing a hydrocarbon feed comprising at least one alkane or alkylaromatic; at least one of dehydrogenating, dehydrocyclizing, and dehydrocyclodimerizing the hydrocarbon feed in a first reactor in the presence of a first catalyst under first reaction conditions to form a first reaction mixture comprising at least one first alkene, aromatic, alkenylaromatic, or mixtures thereof, unreacted alkane or alkylaromatic, and hydrogen; separating the first reaction mixture in a first membrane separation unit using a first small pore microporous inorganic non-metallic membrane with a pore size of less than or equal to 4 Å at a temperature of greater than 500° C. into a first permeate comprising hydrogen and a first retentate comprising the at least one first alkene, aromatic, alkenylaromatic, or mixtures thereof, the unreacted alkane alkylaromatic, and hydrogen, and wherein the first membrane separation unit is separate from the first reactor; heating the first reaction mixture before separating the first reaction mixture in the first membrane separation unit or heating the first retentate after separating the first reaction mixture in the first membrane separation unit; at least one of dehydrogenating, dehydrocyclizing, and dehydrocyclodimerizing the first retentate in a second reactor in the presence of a second catalyst under second reaction conditions to form a second reaction mixture comprising at least one second alkene, aromatic, alkenylaromatic, or mixtures thereof, the at least one first alkene or aromatic or both, unreacted alkane or alkylaromatic, and hydrogen; separating the second reaction mixture in a second membrane separation unit using a second small pore microporous inorganic non-metallic membrane with a pore size of less than or equal to 4 Å at a temperature of greater than 500° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the second membrane separation unit is separate from the second reactor. An embodiment of the invention is one, any or all of prior embodiments in this paragraph up through the first embodiment in this paragraph wherein at least one of the first or second small pore microporous inorganic non-metallic membranes comprises a silica membrane, a ceramic membrane, or a molecular sieve membrane. An embodiment of the invention is one, any or all of prior embodiments in this paragraph up through the first embodiment in this paragraph wherein at least one of the first or second small pore microporous inorganic non-metallic membranes comprises a molecular sieve membrane selected from AlPO-14, AlPO-18, AlPO-34, SAPO-34, a CHA type molecular sieve, SSZ-13, DD3R, ITQ-12, CDS-1, UZM-25, or combinations thereof. An embodiment of the invention is one, any or all of prior embodiments in this paragraph up through the first embodiment in this paragraph wherein at least one of separating the first reaction mixture or separating the second reaction mixture takes place at the temperature of at least 550° C. An embodiment of the invention is one, any or all of prior embodiments in this paragraph up through the first embodiment in this paragraph further comprising heating the second reaction mixture or the second retentate; at least one of dehydrogenating, dehydrocyclizing, and dehydrocyclodimerizing the second retentate in a third reactor in the presence of a third catalyst under third reaction conditions to form a third reaction mixture comprising at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, unreacted alkane or alkylaromatic, and hydrogen; and separating the third reaction mixture in a third membrane separation unit using a third small pore microporous inorganic non-metallic membrane with a pore size of less than or equal to 4 Å at a temperature of greater than 500° C. into a third permeate comprising hydrogen and a third retentate comprising the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the third membrane separation zone is separate from the third reactor. An embodiment of the invention is one, any or all of prior embodiments in this paragraph up through the first embodiment in this paragraph further comprising at least one of dehydrogenating, dehydrocyclizing, and dehydrocyclodimerizing the third retentate in a fourth reactor in the presence of a fourth catalyst under fourth reaction conditions to form a fourth reaction mixture comprising at least one fourth alkene, aromatic, alkenylaromatic, or mixtures thereof, the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, the unreacted alkane or alkylaromatic, and hydrogen. An embodiment of the invention is one, any or all of prior embodiments in this paragraph up through the first embodiment in this paragraph wherein the hydrocarbon feed comprises at least one alkane containing 2 to 12 carbon atoms, and wherein the first reaction mixture comprises the at least one first alkene having a same number of carbon atoms as the at least one alkane in the hydrocarbon feed and wherein the second reaction mixture comprises at least one second alkene having a same number of carbon atoms as the at least one alkane in the hydrocarbon feed. An embodiment of the invention is one, any or all of prior embodiments in this paragraph up through the first embodiment in this paragraph wherein the hydrocarbon feed comprises the at least one alkane containing 2 to 4 carbon atoms; wherein the hydrocarbon feed is dehydrogenated in the first reactor and wherein the reaction conditions include at least one of a temperature in a range of 500 to 1000° C., and pressure in a range of 0 to 1379 kPa; wherein the first reaction mixture comprises at least first one alkene having a same number of carbon atoms as the at least one alkane in the hydrocarbon feed; wherein the first reaction mixture is dehydrogenated in the second reactor and wherein the reaction conditions include at least one of a temperature in a range of 500 to 1000° C., and pressure in a range of 0 to 1379 kPa; and wherein the second reaction mixture comprises at least one second alkene having a same number of carbon atoms as the at least one alkane in the hydrocarbon feed. An embodiment of the invention is one, any or all of prior embodiments in this paragraph up through the first embodiment in this paragraph wherein the hydrocarbon feed comprises the at least one alkane containing 6 to 12 carbon atoms; wherein the hydrocarbon feed is dehydrocyclized in the first reactor, and wherein the reaction conditions include at least one of a temperature in a range of 400 to 650° C., and pressure in a range of 0 to 1379 kPa; wherein the first reaction mixture comprises at least first one aromatic having a same number of carbon atoms as the at least one alkane in the hydrocarbon feed; wherein the reaction mixture is dehydrocyclized in the second reactor, and wherein the reaction conditions include at least one of a temperature in a range of 400 to 650° C., and pressure in a range of 0 to 1379 kPa; and wherein the second reaction mixture comprises at least one second aromatic having a same number of carbon atoms as the at least one alkane in the hydrocarbon feed. An embodiment of the invention is one, any or all of prior embodiments in this paragraph up through the first embodiment in this paragraph wherein the hydrocarbon feed comprises the at least one alkane containing 2 to 7 carbon atoms; wherein the hydrocarbon feed is dehydrocyclodimerized in the first reactor, and wherein the reaction conditions include at least one of a temperature in a range of 400 to 1000° C., and pressure in a range of 0 to 1379 kPa; wherein the reaction mixture is dehydrocyclodimerized in the second reactor, and wherein the reaction conditions include at least one of a temperature in a range of 400 to 1000° C., and pressure in a range of 0 to 1379 kPa. An embodiment of the invention is one, any or all of prior embodiments in this paragraph up through the first embodiment in this paragraph further comprising separating the unreacted alkane or alkylaromatic from at least one of the first reaction mixture and the second reaction mixture. An embodiment of the invention is one, any or all of prior embodiments in this paragraph up through the first embodiment in this paragraph further comprising recycling the separated unreacted alkane or alkylaromatic to at least one of the first reactor and the second reactor. An embodiment of the invention is one, any or all of prior embodiments in this paragraph up through the first embodiment in this paragraph further comprising combining at least one of the first permeate and the second permeate with the unreacted alkane or alkylaromatic; and recycling the combined permeate and unreacted alkane or alkylaromatic to at least one of the first reactor and the second reactor. An embodiment of the invention is one, any or all of prior embodiments in this paragraph up through the first embodiment in this paragraph wherein at least one of the first reaction conditions or the second reaction conditions comprises at least one of a temperature of 400 to 1200° C., a pressure in a range of 0 to 1379 kPa, and a space velocity of 0.1 to 10 hr$^{-1}$ WHSV. An embodiment of the invention is one, any or all of prior embodiments in this paragraph up through the first embodiment in this paragraph wherein the hydrocarbon feed comprises 0 to 70 mol % of hydrogen. An embodiment of the invention is one, any or all of prior embodiments in this paragraph up through the first embodiment in this paragraph wherein an amount of hydrogen removed from the first or second reaction mixture is 20 mol % to 99 mol % of the hydrogen produced in the dehydrogenation, dehydrocyclization, and dehydrocyclodimerization reaction. An embodiment of the invention is one, any or all of prior embodiments in this paragraph up through the first embodiment in this paragraph wherein a purity of the hydrogen in the first or second permeate is 80 mol % or more.

A second embodiment of the invention is a catalytic reactor and membrane separation process comprising providing a hydrocarbon feed comprising at least one alkane or alkylaromatic; at least one of dehydrogenating, dehydrocyclizing, and dehydrocyclodimerizing the hydrocarbon feed in a first reactor in the presence of a first catalyst under first reaction conditions to form a first reaction mixture comprising at least one first alkene, aromatic, alkenylaromatic, or mixtures thereof, unreacted alkane or alkylaromatic, and hydrogen; separating the first reaction mixture in a first membrane separation unit using a first small pore microporous inorganic non-metallic membrane with a pore size of less than or equal to 4 Å at a temperature of greater than 550° C. into a first permeate comprising hydrogen and a first retentate comprising the at least one first alkene, aromatic, alkenylaromatic, or mixtures thereof, the unreacted alkane alkylaromatic, and hydrogen, and wherein the first membrane separation unit is separate from the first reactor; heating the first reaction mixture before separating the first reaction mixture in the first membrane separation unit or heating the first retentate after separating the first reaction mixture in the first membrane separation unit; at least one of dehydrogenating, dehydrocyclizing, and dehydrocyclodimerizing the first retentate in a second reactor in the presence of a second catalyst under second reaction conditions to form a second reaction mixture comprising at least one second alkene, aromatic, alkenylaromatic, or mixtures thereof, the at least one first alkene or aromatic or both, unreacted alkane or alkylaromatic, and hydrogen; separating the second reaction mixture in a second membrane separation unit using a second small pore microporous inorganic non-metallic membrane with a pore size of less than or equal to 4 Å at a temperature of greater than 550° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the second membrane separation unit is separate from the second reactor; wherein at least one of the first or second small pore microporous inorganic non-metallic membranes comprises a molecular sieve membrane selected from AlPO-14, AlPO-18, AlPO-34, SAPO-34, a CHA type molecular sieve, SSZ-13, DD3R, ITQ-12, CDS-1, UZM-25, or combinations thereof. An embodiment of the invention is one, any or all of prior embodiments in this paragraph up through the second embodiment in this paragraph further comprising separating the unreacted alkane or alkylaromatic from at least one of the first reaction mixture and the second reaction mixture, and recycling the separated unreacted alkane or alkylaromatic to at least one of the first reactor and the second reactor. An embodiment of the invention is one, any or all of prior embodiments in this paragraph up through the second embodiment in this paragraph wherein at least one of the first reaction conditions or the second reaction conditions comprises at least one of a temperature of 400 to 1200° C., a pressure in a range of 0 to 1379 kPa, and a space velocity of 0.1 to 10 hr$^{-1}$ WHSV.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A catalytic reactor and membrane separation process comprising:
   providing a hydrocarbon feed comprising at least one alkane or alkylaromatic;
   at least one of dehydrogenating, dehydrocyclizing, and dehydrocyclodimerizing the hydrocarbon feed in a first reactor in the presence of a first catalyst under first reaction conditions to form a first reaction mixture comprising at least one first alkene, aromatic, alkenylaromatic, or mixtures thereof, unreacted alkane or alkylaromatic, and hydrogen;
   separating the first reaction mixture in a first membrane separation unit using a first small pore microporous inorganic non-metallic membrane with a pore size of less than or equal to 4 Å at a temperature of greater than 500° C. into a first permeate comprising hydrogen and a first retentate comprising the at least one first alkene, aromatic, alkenylaromatic, or mixtures thereof, the unreacted alkane alkylaromatic, and hydrogen, and wherein the first membrane separation unit is separate from the first reactor;
   heating the first reaction mixture before separating the first reaction mixture in the first membrane separation unit or heating the first retentate after separating the first reaction mixture in the first membrane separation unit;
   at least one of dehydrogenating, dehydrocyclizing, and dehydrocyclodimerizing the first retentate in a second reactor in the presence of a second catalyst under second reaction conditions to form a second reaction mixture comprising at least one second alkene, aromatic, alkenylaromatic, or mixtures thereof, the at least one first alkene or aromatic or both, unreacted alkane or alkylaromatic, and hydrogen;
   separating the second reaction mixture in a second membrane separation unit using a second small pore microporous inorganic non-metallic membrane with a pore size of less than or equal to 4 Å at a temperature of greater than 500° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the second membrane separation unit is separate from the second reactor.

2. The process of claim 1 wherein at least one of the first or second small pore microporous inorganic non-metallic membranes comprises a silica membrane, a ceramic membrane, or a molecular sieve membrane.

3. The process of claim 1 wherein at least one of the first or second small pore microporous inorganic non-metallic membranes comprises a molecular sieve membrane selected from AlPO-14, AlPO-18, AlPO-34, SAPO-34, a CHA type molecular sieve, SSZ-13, DD3R, ITQ-12, CDS-1, UZM-25, or combinations thereof.

4. The process of claim 1 wherein at least one of separating the first reaction mixture or separating the second reaction mixture takes place at the temperature of at least 550° C.

5. The process of claim 1 further comprising:
   heating the second reaction mixture or the second retentate;
   at least one of dehydrogenating, dehydrocyclizing, and dehydrocyclodimerizing the second retentate in a third reactor in the presence of a third catalyst under third reaction conditions to form a third reaction mixture comprising at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, unreacted alkane or alkylaromatic, and hydrogen; and
   separating the third reaction mixture in a third membrane separation unit using a third small pore microporous inorganic non-metallic membrane with a pore size of less than or equal to 4 Å at a temperature of greater than 500° C. into a third permeate comprising hydrogen and a third retentate comprising the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the third membrane separation zone is separate from the third reactor.

6. The process of claim 5 further comprising at least one of dehydrogenating, dehydrocyclizing, and dehydrocyclodimerizing the third retentate in a fourth reactor in the presence of a fourth catalyst under fourth reaction conditions to form a fourth reaction mixture comprising at least one fourth alkene, aromatic, alkenylaromatic, or mixtures thereof, the at least one third alkene, aromatic, alkenylaromatic, or mixtures thereof, the at least one second alkene, aromatic, alkenylaromatic, or mixtures thereof, the at least one first alkene, aromatic, alkenylaromatic, or mixtures thereof, the unreacted alkane or alkylaromatic, and hydrogen.

7. The process of claim 1 wherein the hydrocarbon feed comprises at least one alkane containing 2 to 12 carbon atoms, and wherein the first reaction mixture comprises the at least one first alkene having a same number of carbon atoms as the at least one alkane in the hydrocarbon feed and wherein the second reaction mixture comprises at least one second alkene having a same number of carbon atoms as the at least one alkane in the hydrocarbon feed.

8. The process of claim 1:
wherein the hydrocarbon feed comprises the at least one alkane containing 2 to 4 carbon atoms;
wherein the hydrocarbon feed is dehydrogenated in the first reactor and wherein the reaction conditions include at least one of a temperature in a range of 500 to 1000° C., and pressure in a range of 0 to 1379 kPa;
wherein the first reaction mixture comprises at least first one alkene having a same number of carbon atoms as the at least one alkane in the hydrocarbon feed;
wherein the first reaction mixture is dehydrogenated in the second reactor and wherein the reaction conditions include at least one of a temperature in a range of 500 to 1000° C., and pressure in a range of 0 to 1379 kPa; and
wherein the second reaction mixture comprises at least one second alkene having a same number of carbon atoms as the at least one alkane in the hydrocarbon feed.

9. The process of claim 1:
wherein the hydrocarbon feed comprises the at least one alkane containing 6 to 12 carbon atoms;
wherein the hydrocarbon feed is dehydrocyclized in the first reactor, and wherein the reaction conditions include at least one of a temperature in a range of 400 to 650° C., and pressure in a range of 0 to 1379 kPa;
wherein the first reaction mixture comprises at least first one aromatic having a same number of carbon atoms as the at least one alkane in the hydrocarbon feed;
wherein the reaction mixture is dehydrocyclized in the second reactor, and wherein the reaction conditions include at least one of a temperature in a range of 400 to 650° C., and pressure in a range of 0 to 1379 kPa; and
wherein the second reaction mixture comprises at least one second aromatic having a same number of carbon atoms as the at least one alkane in the hydrocarbon feed.

10. The process of claim 1:
wherein the hydrocarbon feed comprises the at least one alkane containing 2 to 7 carbon atoms;
wherein the hydrocarbon feed is dehydrocyclodimerized in the first reactor, and wherein the reaction conditions include at least one of a temperature in a range of 400 to 1000° C., and pressure in a range of 0 to 1379 kPa;
wherein the reaction mixture is dehydrocyclodimerized in the second reactor, and wherein the reaction conditions include at least one of a temperature in a range of 400 to 1000° C., and pressure in a range of 0 to 1379 kPa.

11. The process of claim 1 further comprising:
separating the unreacted alkane or alkylaromatic from at least one of the first reaction mixture and the second reaction mixture.

12. The process of claim 11 further comprising:
recycling the separated unreacted alkane or alkylaromatic to at least one of the first reactor and the second reactor.

13. The process of claim 11 further comprising:
combining at least one of the first permeate and the second permeate with the unreacted alkane or alkylaromatic; and
recycling the combined permeate and unreacted alkane or alkylaromatic to at least one of the first reactor and the second reactor.

14. The process of claim 1 wherein at least one of the first reaction conditions or the second reaction conditions comprises at least one of a temperature of 400 to 1200° C., a pressure in a range of 0 to 1379 kPa, and a space velocity of 0.1 to 10 $hr^{-1}$ WHSV.

15. The process of claim 1 wherein the hydrocarbon feed comprises 0 to 70 mol % of hydrogen.

16. The process of claim 1 wherein an amount of hydrogen removed from the first or second reaction mixture is 20 mol % to 99 mol % of the hydrogen produced in the dehydrogenation, dehydrocyclization, and dehydrocyclodimerization reaction.

17. The process of claim 1 wherein a purity of the hydrogen in the first or second permeate is 80 mol % or more.

18. A catalytic reactor and membrane separation process comprising:
providing a hydrocarbon feed comprising at least one alkane or alkylaromatic;
at least one of dehydrogenating, dehydrocyclizing, and dehydrocyclodimerizing the hydrocarbon feed in a first reactor in the presence of a first catalyst under first reaction conditions to form a first reaction mixture comprising at least one first alkene, aromatic, alkenylaromatic, or mixtures thereof, unreacted alkane or alkylaromatic, and hydrogen;
separating the first reaction mixture in a first membrane separation unit using a first small pore microporous inorganic non-metallic membrane with a pore size of less than or equal to 4 Å at a temperature of greater than 550° C. into a first permeate comprising hydrogen and a first retentate comprising the at least one first alkene, aromatic, alkenylaromatic, or mixtures thereof, the unreacted alkane alkylaromatic, and hydrogen, and wherein the first membrane separation unit is separate from the first reactor;
heating the first reaction mixture before separating the first reaction mixture in the first membrane separation unit or heating the first retentate after separating the first reaction mixture in the first membrane separation unit;
at least one of dehydrogenating, dehydrocyclizing, and dehydrocyclodimerizing the first retentate in a second reactor in the presence of a second catalyst under second reaction conditions to form a second reaction mixture comprising at least one second alkene, aromatic, alkenylaromatic, or mixtures thereof, the at least one first alkene or aromatic or both, unreacted alkane or alkylaromatic, and hydrogen;
separating the second reaction mixture in a second membrane separation unit using a second small pore microporous inorganic non-metallic membrane with a pore size of less than or equal to 4 Å at a temperature of greater than 550° C. into a second permeate comprising hydrogen and a second retentate comprising the at least one second alkene, aromatic, alkenylaromatic, or mixtures thereof, the at least one first alkene, aromatic, alkenylaromatic, or mixtures thereof, the unreacted alkane or alkylaromatic, and hydrogen, and wherein the second membrane separation unit is separate from the second reactor;

wherein at least one of the first or second small pore microporous inorganic non-metallic membranes comprises a molecular sieve membrane selected from AlPO-14, AlPO-18, AlPO-34, SAPO-34, a CHA type molecular sieve, SSZ-13, DD3R, ITQ-12, CDS-1, UZM-25, or combinations thereof.

19. The process of claim 18 further comprising:

separating the unreacted alkane or alkylaromatic from at least one of the first reaction mixture and the second reaction mixture, and recycling the separated unreacted alkane or alkylaromatic to at least one of the first reactor and the second reactor.

20. The process of claim 18 wherein at least one of the first reaction conditions or the second reaction conditions comprises at least one of a temperature of 400 to 1200° C., a pressure in a range of 0 to 1379 kPa, and a space velocity of 0.1 to 10 $hr^{-1}$ WHSV.

* * * * *